(12) United States Patent
Asher

(10) Patent No.: US 11,598,697 B2
(45) Date of Patent: Mar. 7, 2023

(54) AIR SAMPLE COLLECTION APPARATUS AND METHODS FOR USE

(71) Applicant: University Corporation for Atmospheric Research, Boulder, CO (US)

(72) Inventor: Elizabeth Asher, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 490 days.

(21) Appl. No.: 16/406,886

(22) Filed: May 8, 2019

(65) Prior Publication Data

US 2020/0355580 A1 Nov. 12, 2020

(51) Int. Cl.
| | | |
|---|---|---|
| *G01N 1/22* | (2006.01) | |
| *G01N 33/00* | (2006.01) | |
| *G01N 1/14* | (2006.01) | |
| G01N 1/02 | (2006.01) | |
| G01N 1/20 | (2006.01) | |

(52) U.S. Cl.
CPC ............... *G01N 1/22* (2013.01); *G01N 1/14* (2013.01); *G01N 33/0004* (2013.01); *G01N 2001/021* (2013.01); *G01N 2001/1427* (2013.01); *G01N 2001/2071* (2013.01); *G01N 2001/222* (2013.01)

(58) Field of Classification Search
CPC ........ G01N 1/22; G01N 33/0004; G01N 1/14; G01N 2001/222; G01N 2001/1427; G01N 2001/021; G01N 2001/2071; G01N 1/2205; G01N 1/2202; G01N 1/2273; G01N 1/2279; G01N 1/24

USPC ..... 73/31.01, 31.02, 863.31, 863.71, 863.72, 73/863.73, 864.31, 864.34

See application file for complete search history.

(56) References Cited

U.S. PATENT DOCUMENTS

| | | | | |
|---|---|---|---|---|
| 5,553,508 A | * | 9/1996 | Dabberdt | G01N 1/2273 |
| | | | | 73/863.02 |
| 6,012,487 A | * | 1/2000 | Hauck | F16K 11/0743 |
| | | | | 137/625.11 |
| 8,840,852 B2 | * | 9/2014 | Bouchentouf | G01N 35/1097 |
| | | | | 422/538 |
| 10,330,571 B2 | * | 6/2019 | Adams | G01N 1/2273 |
| 2008/0229805 A1 | * | 9/2008 | Barket | G01N 1/2214 |
| | | | | 73/31.01 |
| 2011/0088490 A1 | * | 4/2011 | Ludwick | G01N 1/2273 |
| | | | | 73/863.11 |
| 2019/0204189 A1 | * | 7/2019 | Mohr, Jr. | G05D 1/0646 |

* cited by examiner

*Primary Examiner* — Robert R Raevis
(74) *Attorney, Agent, or Firm* — The Ollila Law Group LLC

(57) ABSTRACT

An air sample collection apparatus and methods for operating the air sample collection apparatus are provided. The air sample apparatus comprises a plurality of air canisters comprising at least a first canister and a second canister, a multi-position valve comprising an outlet, and an inlet region, which are fluidly connected to a plurality of ports. Each respective port is fluidly connected to a canister of the plurality of air canisters, a pump operable to provide pressurized sample air to the inlet region of the multi-position valve, and a computing device operable to open and close each respective port fluidly coupled to each canister of the plurality of canisters.

23 Claims, 6 Drawing Sheets

AIR SAMPLE COLLECTION APPARATUS AND METHODS FOR USE

GOVERNMENT LICENSE RIGHTS

This invention was made with Government support under awards M0856145 awarded by the National Science Foundation. The Government has certain rights in this invention.

TECHNICAL FIELD

The present Application is directed towards an air sample collection apparatus, and more particularly, to a canister air sample collection apparatus.

BACKGROUND

Volatile Organic Compounds (VOCs) are ubiquitous in the atmosphere and consist of several subgroups or classes including non-methane hydrocarbons (NMHC), oxygenated VOCs (OVOCs) and halogenated VOCs (HVOCs). The production of ozone and other photooxidants and particulate matter by reactions of VOCs and NOx is recognized as a serious global environmental problem. Other VOCs are directly emitted air toxics.

There is a need for higher resolution determination of the mass flux balance of VOCs. In order to generate mass flux data, it is necessary to generate measurements of VOC concentrations or mixing ratios and wind measurements at a series of positions, for example for multiple latitude and longitude coordinates or for a profile of altitudes. Preferably, the mass flux would be measured for a wide range of VOC species. With higher quality mass flux VOC data, it may be possible to better identify and quantify distinct industrial and natural sources of pollution, for example pollution from oil and natural gas production, and determine how that pollution is being transported through the planetary boundary layer. Improved VOC flux data could be further used to validate atmospheric models of the turbulent atmospheric boundary layer for air quality forecasting of ozone, particulates, and other air toxins, and for long-term global monitoring of atmospheric trace gasses.

Lightweight air sampling instruments paired with small, unmanned aerial systems (UASs) have the potential vastly increase VOC flux data and concentration measurements. However, the identification and quantification of a wide range of atmospheric VOCs species has previously been performed using different techniques, some of which are tailored to the analysis of only a few species or face other limitations. For instance, several prior methods suffer from long sample collection times and only a few samples per flight.

Prior methods of measuring atmospheric trace gasses include the AirCore Sampling system. The AirCore sampling system comprises a long, tightly wound single tube with a small inner diameter launched via balloon. During the descent, sample air flows into the tube, and a valve closes when the AirCore lands to seal the sample gas inside. While the AirCore Sampling system is able to separate and identify long-lived greenhouse gases such as CH4, CO2, and CO, the AirCores small inner diameter limits its usefulness for detecting a wide range of VOCs. In addition, the AirCore provides very small gas sample sizes, which may not provide an adequate signal to noise ratio for many applications.

Prior methods also include installing a single two-liter evacuated stainless steel canister on a helicopter to collect gas samples. The canister is opened automatically or remotely at altitude and allowed to fill with ambient sample air. The air sample collected is limited by turbulence due to helicopter rotor wash. In addition, because the two-liter vacuum canister has a long fill time, it also provides for poor spatial sampling.

Other prior methods include the use of a filtered, VOC-absorbent cartridge system. The VOC-absorbent cartridge system is used to absorb trace gasses, which may be later evaluated via gas chromatography in a lab. Desorption of VOCs from the cartridges can lead to measurement artifacts, high blanks, and high detection limits, however. Moreover, VOC-absorbent cartridge systems require long integrations, 10 minutes per sample. Much like the other methods, the cartridge system provides for poor spatial resolution.

As unmanned aerial systems (UASs) become more common, they represent a possible way to obtain VOC data more quickly and for lower cost over balloons and manned aircraft. Many prior methods include equipment that is too heavy or bulky to fly on low cost UASs, however. In addition, the prior methods are ill equipped to deal with rotor washout eddies and turbulence caused by the UAS copter blades, which can introduce sampling artifacts and obstruct ambient housekeeping measurements of the atmosphere. Many of these methods are also without accurate housekeeping measurements that could be used to help determine background meteorological conditions to help interpret the VOC measurements.

What is needed is a system with faster air sampling to obtain measurements more quickly, the ability to obtain multiple samples that may be resolved over multiple locations, the ability to obtain ambient air samples and wind samples that are not subject to rotor washout, and a system that is also light weight, more compact, and easier to use.

SUMMARY

An air sample collection apparatus is provided. The air sample collection apparatus comprises a plurality of air canisters comprising at least a first canister and a second canister, a multi-position valve comprising an outlet, and an inlet region fluidly connected to a plurality of ports, each respective port fluidly connected to a canister of the plurality of air canisters, a pump operable to provide pressurized sample air to the inlet region of the multi-position valve, and a computing device operable to open and close each respective port fluidly coupled to each canister of the plurality of canisters.

A first method for collecting air samples using an air sample collection apparatus is provided. The air sample collection apparatus comprises a plurality of air canisters including at least a first canister and a second canister, a multi-position valve comprising an outlet, and an inlet region fluidly connected to a plurality of ports, each respective port fluidly connected to a canister of the plurality of air canisters, a pump operable to provide pressurized sample air to the inlet region of the multi-position valve, and a computing device operable to open and close each respective port fluidly coupled to each canister of the plurality of canisters. The method comprises operating the pump to provide pressurized sample air to the inlet region of the multi-position valve, opening a first respective port of the multi-position valve to the first canister, upon filling the first canister with the pressurized sample air, closing the first respective port of the multi-position valve to the first canister, opening a second respective port to the second canister, and upon filling the second canister with the pressurize sample air, closing the second respective port to the second canister.

A second method for collecting air samples using an air sample collection apparatus on an unmanned aerial system (UAS) is provided. The air sample collection apparatus comprises a plurality of air canisters including at least a first canister and a second canister, a multi-position valve comprising an outlet, and an inlet region fluidly connected to a plurality of ports, each respective port fluidly connected to a canister of the plurality of air canisters, a pump operable to provide pressurized sample air to the inlet region of the multi-position valve, and a computing device operable to open and close each respective port fluidly coupled to each canister of the plurality of canisters. The method comprises positioning the UAS at a first position, opening a first respective port of the multi-position valve to the first canister, upon filling the first canister with the pressurized sample air, closing the first respective port of the multi-position valve to the first canister, positioning the UAS at a second position, opening a second respective port to the second canister, and closing the second respective port to the second canister.

BRIEF DESCRIPTION OF THE DRAWINGS

The same reference number represents the same element on all drawings. The drawings are not necessarily to scale.

DETAILED DESCRIPTION

FIGS. 1-6 and the following description depict specific examples to teach those skilled in the art how to make and use the best mode of the Application. For the purpose of teaching inventive principles, some conventional aspects have been simplified or omitted. Those skilled in the art will appreciate variations from these examples that fall within the scope of the Application. Those skilled in the art will appreciate that the features described below may be combined in various ways to form multiple variations of the Application. As a result, the Application is not limited to the specific examples described below, but only by the claims and their equivalents.

Figure 1:
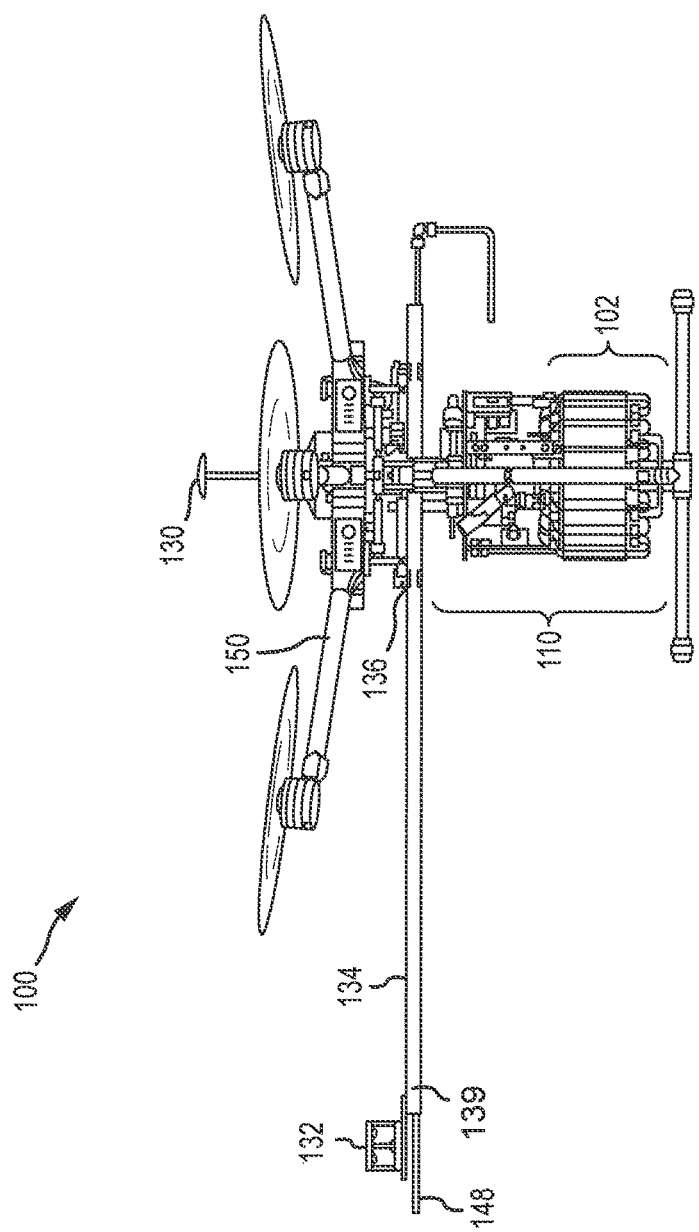
FIG. 1 depicts air sample collection system 100, in accordance with an embodiment.

FIG. 1 depicts air sample collection system 100, in accordance with an embodiment. Air sample collection system 100 comprises an air sample collection apparatus integrated as a payload on an unmanned aerial system (UAS) 150. The depiction of air sample collection apparatus 300 integrated onto UAS 150 is not intended to be limiting, however. In further embodiments, air sample collection apparatus may be integrated onto any type of vehicle known to those of skill, or not integrated onto a vehicle at all.

Air sample collection apparatus 300 may be used to collect multiple whole air samples, or any type of fluid sample known to those of skill. Air sample collection apparatus 300 includes a plurality of air canisters 102, a multi-position valve 108, a pump 118, and a computing device 120.

Figure 2:
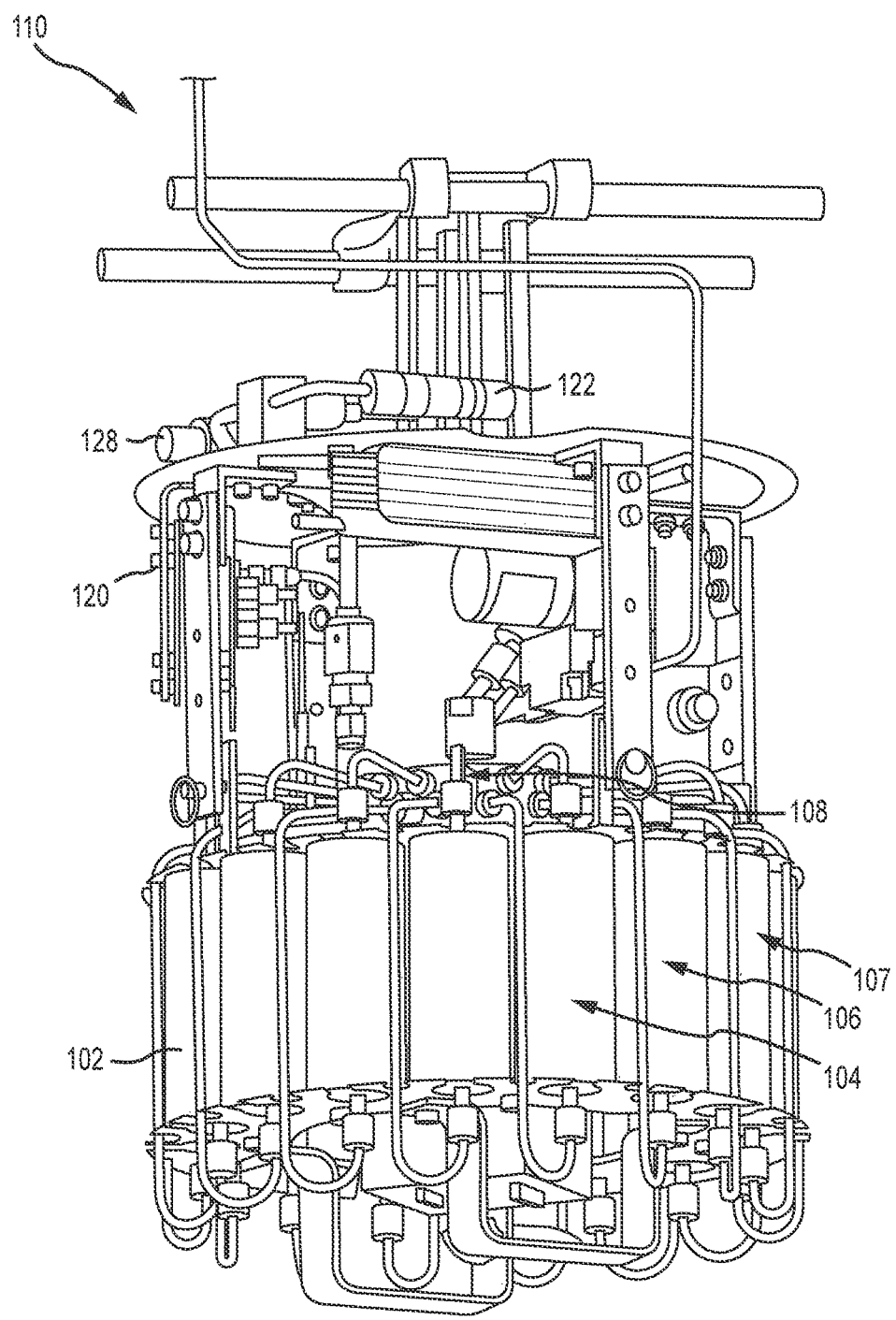
FIG. 2 depicts air canister array assembly 110, in accordance with an embodiment.
Figure 3:
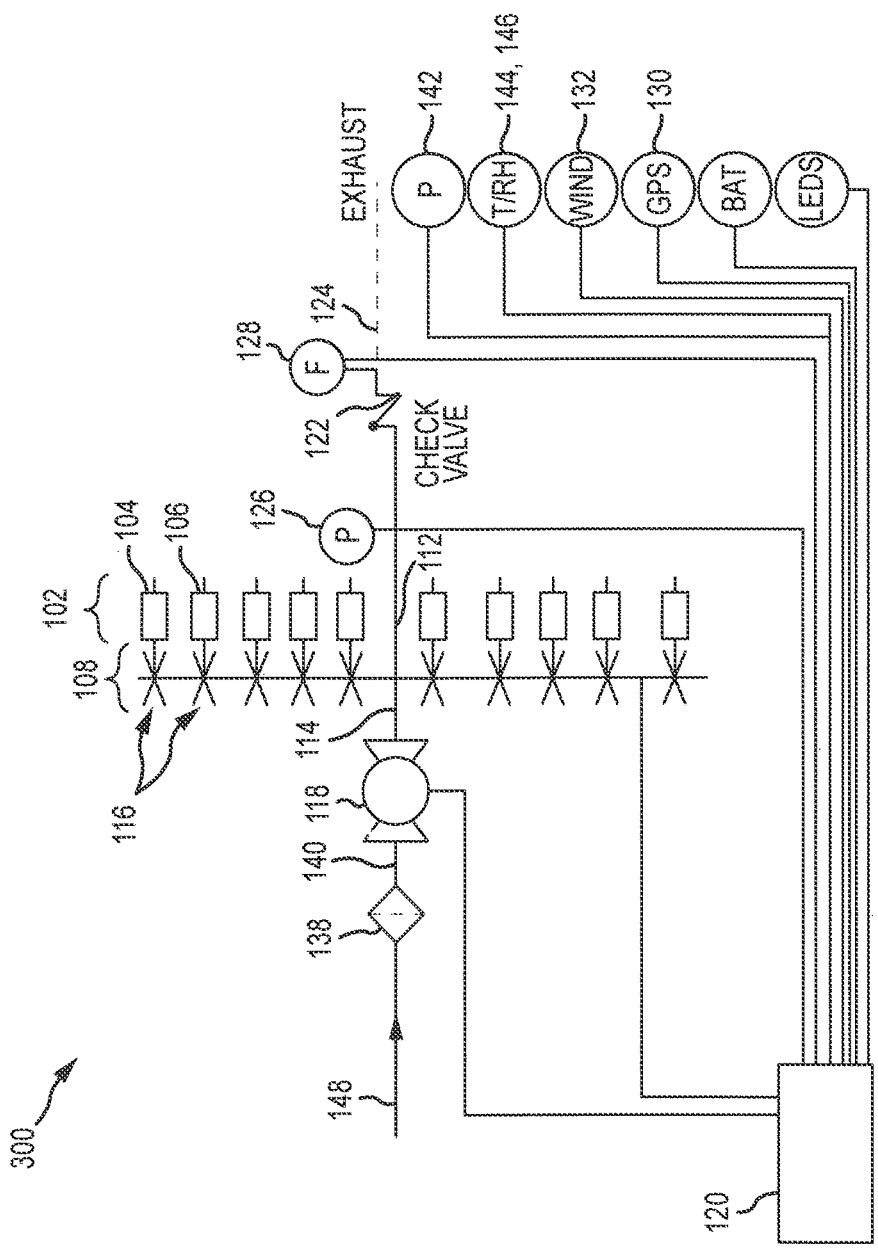
FIG. 3 depicts air sample collection apparatus 300, in accordance with an embodiment.
Figure 4:
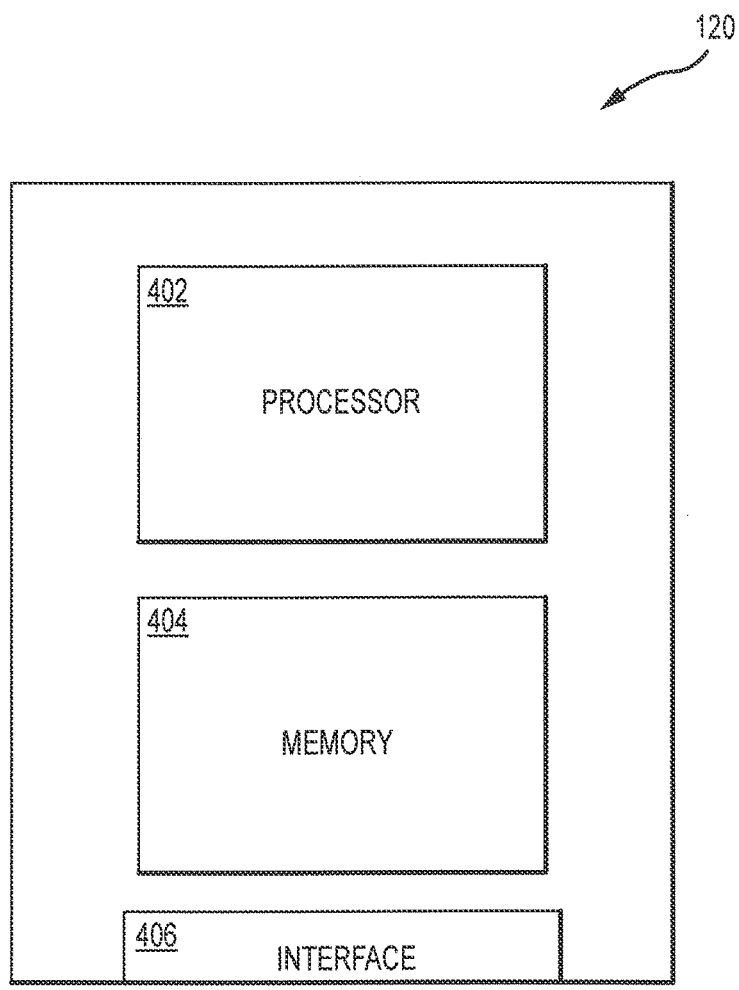
FIG. 4 depicts computing device 120, in accordance with an embodiment.

FIGS. 2-4 depict further details of air sample collection apparatus 300: FIG. 2 depicts air canister array assembly 110; FIG. 3 depicts a block diagram of air sample collection apparatus 300; and FIG. 4 depicts computing device 120.

As may be seen in FIGS. 1 and 2, plurality of air canisters 102 includes at least a first canister 104 and a second canister 106. The first and second canisters 104, 106 of the plurality of air canisters 102 may be opened and closed to collect an air sample. The first and second canisters 104, 106 of the plurality of air canisters 102 may be further opened and closed to allow for analysis of a previously collected air sample. In embodiments, plurality of air canisters 102 may include any number of canisters.

Canisters 104, 106 may be filled with sample air and subsequently transported to a lab site for evaluation. In embodiments, canisters 104, 106 may be flushed and reused to collect new samples. In embodiments, each canister of the plurality of air canisters 102 may be used to collect air samples at a different respective location, thereby providing for sampling over a range of spatial locations.

In examples, the plurality of canisters 102 may comprise miniaturized custom fabricated cylindrical canisters with a volume of approximately 100 mL. The relatively low canister volume may allow for air sample collection apparatus 300 to be relatively light weight. It may further allow for quick filling of the air canisters in flight. In other embodiments, however, other sizes and formats of air canister are possible, as will be understood by those of skill.

Multi-position valve 108 comprises an outlet 112 and an inlet region 114 fluidly connected to a plurality of ports 116. Inlet region 114 is coupled to the plurality of ports 116 and is further fluidly coupled to an additional inlet 148. Outlet 112 is fluidly coupled to the inlet region 114. Multi-position valve 108 is operable to open the ports of the plurality of ports 116. In embodiments, multi-position valve 108 may be operable to open only one port at a time. In further embodiments, however, multi-position valve 108 may be operable to open more than one port.

Opening a port of the plurality of ports 116 fluidly couples the fluid contents of a respective canister positioned at the respective port to the inlet region 114. In embodiments, there may be a canister connected to every port of the plurality of ports 116. In further embodiments, however, there may be fewer canisters than ports. In the case where there are fewer canisters than ports, the ports without a canister connected may be fluidly connected to other fluid supplies, capped, or open to the ambient air.

Air sample collection apparatus 300 further comprises pump 118. Pump 118 is operable to provide pressurized sample air to inlet region 114 of multi-position valve 108. In examples, pump 118 may pressurize ambient air, whole air, or any fluid supplied to the inlet region 114 via inlet 148. In embodiments, pump 118 may provide a positive differential pressure so that the inlet region 114 has a pressure is at least 10 psi greater than the pressure at inlet 148. In further embodiments, however, pump 118 may provide any level of positive pressurization to fluid introduced via inlet 148.

By pressurizing the air enclosed in each canister of the plurality of canisters 102 using pump 118, it may be possible to fill the canisters more quickly with a greater quantity of sample air. Operators may therefore acquire air samples over a range of positions more quickly. Pressurizing the canister may also help increase the sample size for later analysis, enabling the operator to analyze two or more subsamples from each canister in the plurality of canisters in its current embodiment, and potentially more subsamples in future embodiments. As a result, pressurizing the canisters may help support a broader species analysis and better statistics with a gas chromatograph, for example.

Air sample collection apparatus 300 further comprises a computing device 120. Computing device 120 is operable to open and close each respective port fluidly coupled to each canister 104, 106 of the plurality of canisters 102.

FIG. 4 depicts example computing device 120 in accordance with an embodiment. Computing device 120 includes a processor 402, a memory 404, and an interface 406. Computing device 120 may execute one or more routines to operate air sample collection apparatus 300 to facilitate collecting air samples, analyzing air samples, or obtaining further science or housekeeping data.

Interface 406 is connected to the multi-position valve 108 and the pump 118. Interface 406 may be further connected to various other hardware components or housekeeping sensors comprising air sample collection apparatus 300. For example, interface 406 pressure sensors, flow meter sensors, mass flow controllers, a global positioning system sensor, pressure sensors, wind sensors, temperature or humidity sensors, further valves, or any other type of sensor or mechanism known to those of skill.

Interface 406 may enable communications between processor 402 and external devices. Interface 406 may be capable of any manner of electronic, optical, or wireless communication.

Processor 402 executes one or more processing routines, such as, for example, methods 600 and 700 described below. Processor 402 may be further operable to command other operations for, or processes data received from air sample collection apparatus 300.

Processor 402 may comprise a general-purpose computer, a micro-processing system, a logic circuit, a field programmable logic array (FPGA), or any other general purpose or customized processing device capable of performing the functions described herein. In embodiments, processor 402 may be distributed among multiple processing devices.

Memory 404 may comprise a primary or main memory, such as a random access memory (RAM). Memory 404 may store operational parameters and data, software routines, constant values, and variable values. Memory 404 may store variables that may be used by methods 500 or 600 to operate air sample collection apparatus 300. Memory 404 may also store instructions to execute methods 500 or 600.

It should be understood that computing device 120 may include various other components and functions that are generally known in the art. These additional features are omitted from the description and the figures for the purpose of brevity. Therefore, the present invention should not be limited to the specific embodiments shown and discussed.

In embodiments, air sample collection apparatus 300 may further comprise a check valve 122 fluidly coupled to the inlet region 114 of the multi-position valve 108. Check valve 122 may be operable to exhaust fluid over a minimum crack pressure to an exhaust 124. Along with pump 118, check valve 122 may help to further regulate the pressurized sample air within inlet region 114 at the minimum crack pressure. In further embodiments, however, other techniques may be used to regulate the pressurized sample air within inlet region 114, as will be understood by those of skill in the art.

In embodiments, air sample collection apparatus 300 may further comprise a sample pressure sensor 126 fluidly coupled to the inlet region 114 of the multi-position valve 108. In examples, sample pressure sensor 126 may comprise a differential pressure sensor, or an absolute pressure sensor. Sample pressure sensor 126 may be used to provide feedback during a canister filling operation, or to provide information about canister pressurization in post-processing. Computing device 120 may receive data from sample pressure sensor 126 via interface 406.

In embodiments, air sample collection apparatus 300 may further comprise a flow meter 128 coupled to the exhaust of the check valve 122. In embodiments, flow meter 128 may be fluidly coupled to exhaust 124. In embodiments, flow meter 128 may be used to determine a mass flow rate, a volume flow rate, or a density of the fluid being sampled. Flow meter 128 may help determine how much fluid has flushed out of inlet region 114 and any respective air canister used to collect an air sample. This may be helpful to help determine, either while the respective air canister is being filled or after the fact in post-processing, whether the canister has undergone a sufficient number of fluid flushes before the respective port of the multi-position valve seals the canister to encapsulate sample air for later analysis. Computing device 120 may receive data from flow meter 128 via interface 406.

In embodiments, air sample collection apparatus 300 may further comprise a global positioning system (GPS) 130. GPS 130 may provide data to computing device 120 via interface 406, which in embodiments may be used to execute any of the steps of methods 600 and 700. GPS 130 may be used in post-processing to determine the exact locations where individual air canisters of the plurality of air canisters 102 were filled with sample air and determine that the air sample collection apparatus 300 may have reached an approximate pre-determined location to initiate filling of an individual air canister of the plurality of canisters 102. In further embodiments, two-way radio or cellular communication to the UAS may also initiate air sample collection during flight.

In embodiments, air sample collection apparatus 300 may further comprise an anemometer 132. Anemometer 132 may be used to determine a wind direction and/or wind speed in one or more directions. In embodiments, anemometer 132 may be used to determine the wind direction and wind speed in two directions in the horizontal plane. Wind data received with anemometer 132 may further help air sample collection apparatus 300 operators determine VOC mass flux.

In embodiments, air sample collection apparatus 300 may further include a boom 134 comprising a coupled end and a distal end, with the anemometer being coupled to the distal end of the boom. Boom 134 is depicted in FIG. 1, where it may be seen that anemometer 132 is positioned at a distal end 139 of boom 134. The coupled end 136 of boom 134 is coupled to UAS 150. In embodiments, boom 134 may extend at least 4.5 feet from the coupled end 136 to the distal end 139. By positioning the anemometer 132 at least 4.5 feet from coupled end 136, it may be possible to provide wind speed and/or wind direction data that is not disrupted by the turbulent airflow generated by the multi-rotor UAS platform. Field experiments comprising flying a UAS 150 with temperature, relative humidity, and pressure sensors mounted at least 4.5 feet from the coupled end 136 on distal end 139 of boom 134 have confirmed that 4.5 feet is outside of the envelope of UAS 150 rotor turbulence. In other words, instruments such as anemometer 132 which are placed on a boom 4.5 feet from coupled end 136 appear to experience a well-mixed atmospheric boundary layer conditions.

In further embodiments, however boom 134 may be any length that allows wind direction and wind speed to be sampled outside of the turbulent airflow caused by the rotors of a UAS platform, as will be understood by those of skill.

In embodiments, inlet 148 may be positioned on distal end 139 of boom 134, as depicted in FIG. 1. This may further allow for air sampling to take place outside the envelope of rotor turbulence.

In embodiments, plurality of canisters 102 may further comprise at least a third canister 107, similar to first and second canisters 104, 106. The plurality of air canisters 102 may further be positioned in a circumferential arrangement. For example, FIG. 2 depicts air canister assembly 110. Air canister assembly 110 includes first, second, and third canisters 104, 106, and 107, in addition to several other air canisters positioned in a circumferential arrangement. The circumferential arrangement may provide for a compact assembly that takes up less space on a UAS, particularly when plurality of canisters 102 must be coupled between the legs of a UAS. It may further allow for less tubing between the individual canisters and a centrally positioned multi-position valve 108, allowing air canister assembly 110 to be lighter weight for integration onto an inexpensive, commercial UAS.

In embodiments, air sample collection apparatus 300 may further comprise a filter 138 coupled to an inlet 140 of the pump 118, operable to remove particles from fluid entering the pump 118. For example, filter 118 may comprise a Swagelok 2 μm filter. The use of filter 138 may help prevent contamination of the plurality of canisters 102, pump 118, and inlet region 114.

In embodiments, air sample collection apparatus 300 may further comprise at least one of: an ambient pressure sensor 142, an ambient temperature sensor 144, a relative humidity sensor, or an ambient relative humidity sensor 146. In embodiments, these sensors may be integrated onto any available position on UAS 150 or air canister assembly 110. In further embodiments, one or more of ambient pressure sensor 142, ambient temperature sensor 144, relative humidity sensor 146, or ambient relative humidity sensor 146 may be placed at distal end 139 of boom 134 to provide measurements outside the turbulence of UAS 150 at least during vertical assents. One or more olaf ambient pressure sensor 142, ambient temperature sensor 144, relative humidity sensor 146, or ambient relative humidity sensor 146 may be used to determine whether a sample location is part of the well-mixed atmospheric boundary layer, or to provide further context for the VOC data extracted from the fluid inside of plurality of canisters 102. In further embodiments two-way radio or cellular communication may transfer these housekeeping data processed in near real-time to operator.

Figure 5:
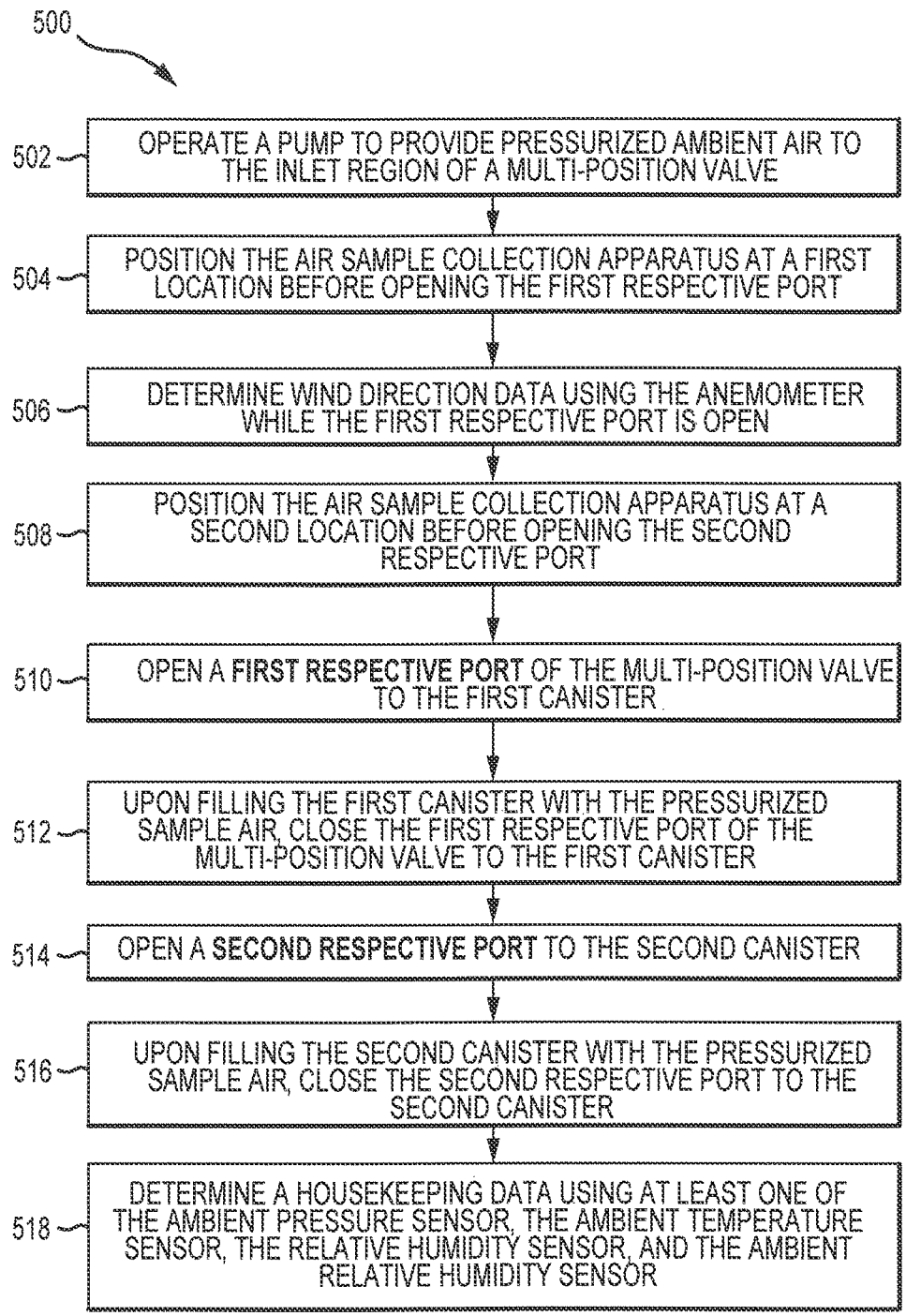
FIG. 5 depicts method 500, in accordance with an embodiment.

FIG. 5 depicts method 500, in accordance with an embodiment. Method 500 describes a procedure to collect air samples using air sample collection apparatus 300.

Method 500 includes steps 502, 510, 512, 514, 516. In further embodiments, however, method 500 may further comprise any combination of steps 504, 506, 508, or 518, as will be further described below.

Method 500 begins with step 502. In step 502, a pump is operated to provide pressurized sample air to the inlet region of the multi-position valve. For example, pump 118 may provide pressurized sample air to inlet region 114 of plurality of canisters 102, as described above. In embodiments, pump 118 may pressurize sample air to a greater pressure than the ambient air being sampled. For example, pump 118 may pressurize the sample air to >10 psi over the ambient pressure, providing a flow rate of at least 1 liter per minute. Pump 118 may provide any amount of pressurization and air flow, however, as will be understood by those of skill.

Method 500 continues with step 510. In step 510, a first respective port of the multi-position valve to the first canister is opened. For example, the first respective port 116 for first canister 104 may be opened. This may allow the air inside first canister 104 to exchange with the pressurized sample air inside of inlet region 114. Eventually, if the first respective port of the multi-position valve 102 is left open long enough, prior contents of first canister 104 will be flushed and first canister 104 will be filled with pressurized sample air.

Method 500 continues with step 512. In step 512, the first respective port of the multi-position valve to the first canister is closed upon filling the first canister with the pressurized sample air. For example, first respective port 116 for first canister 104 may be closed.

In embodiments of step 512, computing device 102 may close the first canister 104 upon the expiration of a predetermined fill period. The predetermined fill period may comprise the length of time required to substantially flush the prior fluid contained in first canister 104 and ensure that first canister 104 is substantially filled with pressurized sample air. For example, if first canister 104 has a volume of 100 mL, pump 118 provides pressurized sample air at a flow of 1 liter per minute at a differential pressure of at least 10 psi, predetermined fill period may be 1.5 minutes. This may allow nine flushes of fluid within first canister 104, so that operators may be substantially certain that all of the fluid contained in first canister 104 is sample air.

In further embodiments of step 512, however, computing device 102 may close the first canister 104 upon determining via feedback that a sufficient number of flushes have occurred within first air canister 104, thereby ensuring that the fluid contained in first canister 104 substantially comprises sample air. For example, computing device 102 may monitor flow meter 128 to assess when a predetermined number of fluid flushes have taken place since the opening of the port corresponding to the first canister 104.

Method 500 continues with step 514. In step 514, a second respective port to the second canister is opened. Step 514 is like step 506, except that it is performed on second canister 106.

Method 500 continues with step 516. In step 516, the second respective port to the second canister is closed upon filling the second canister with the pressurized sample air. Step 516 is like step 512, except that it is performed on second canister 106.

In examples, method 500 may include further steps. For example, method 500 may include step 504. In step 504, the air sample collection apparatus may be positioned at a first position before opening the first respective port. The first position may comprise any combination of geographical location, meaning a location with any latitude and longitude coordinates, or altitude. In embodiments, air sample collection apparatus 300 may be transported to first position via any method known to those of skill, including, but not limited to: a UAS, balloon, helicopter, or a surface vehicle.

In examples, method 500 may further include step 506. In step 506 the air sample collection apparatus may further comprise an anemometer, and wind direction and/or wind speed data may be determined using the anemometer while the first respective port is open. For example, air sample collection apparatus 300 may include anemometer 132, as described above.

In embodiments, the wind direction and/or wind speed data may be saved by computing device 120 on memory 404 to be correlated with air sample composition data later in post-processing.

In examples, method 500 may further include step 508. In step 508 the air sample collection apparatus may be positioned at a second position before opening the second respective port. In embodiments, second position may have any one of a different geographical location or a different altitude from the first position. By using a first position to fill first canister 104 and a second position to fill second canister 106, it may be possible to get air sample composition data over a range of positions.

Because air canister collection apparatus 300 can fill sequential canisters quickly using pump 118, this may allow air canister collection apparatus 300 to collect samples over a number of different locations quickly, providing data that may be used to determine VOC mass flux.

In examples, method 500 may further include step 518. In step 518 the air sample collection apparatus 300 may further comprise at least one of: an ambient pressure sensor, an ambient temperature sensor, a relative humidity sensor, or an ambient relative humidity sensor, and a housekeeping data may be determined using at least one of the ambient pressure sensor, the ambient temperature sensor, the relative humidity sensor, or the ambient relative humidity sensor. The housekeeping data, which may be received at computing device 120 over interface 406 and saved in memory 404, may be used to determine background atmospheric conditions for the samples collected. In examples, the housekeeping data could be transferred to an operator in near-real time using two-way cellular or radio communication.

In embodiments of method 500, the air sample collection apparatus may further comprise a check valve fluidly coupled to the inlet region of the multi-position valve, operable to exhaust fluid over a minimum crack pressure to an exhaust. For example, air sample collection apparatus 300 includes check valve 122, for which the benefits are described above.

Figure 6:
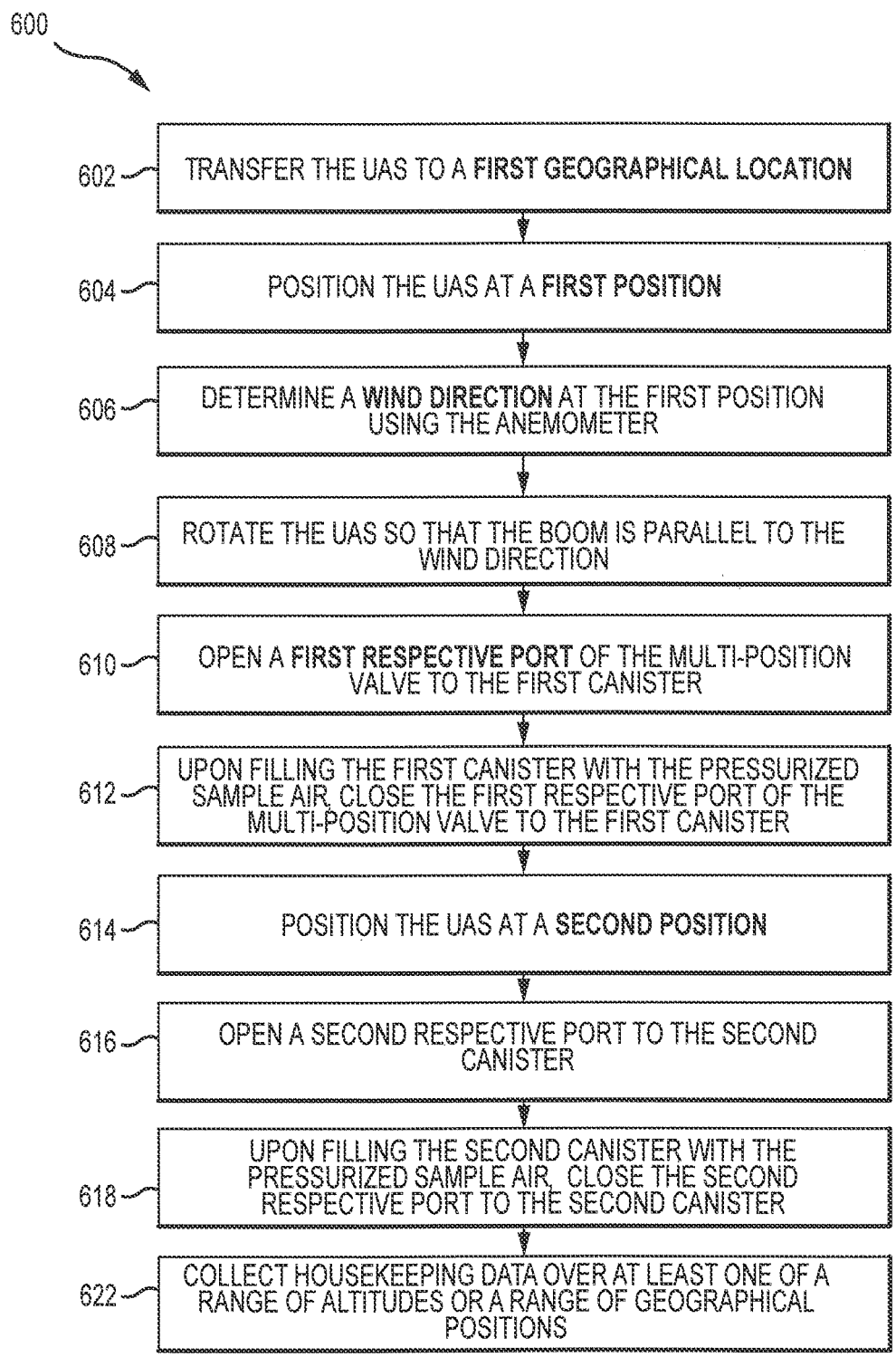
FIG. 6 depicts method 600, in accordance with an embodiment.

FIG. 6 depicts method 600, in accordance with an embodiment. Method 600 may be used to collect air samples using air sample collection apparatus 300 integrated onto a UAS 150.

Method 600 includes steps 604, 610, 612, 614, 616, and 618. In further embodiments, however, method 600 may further comprise any combination of steps 602, 606, 608, 620, or 622, as will be further described below.

Method 600 begins with step 604. In step 604, the UAS is positioned at a first position. In examples, an operator may command UAS 150 to the first position using any commonly used commercial method.

Method 600 continues with step 610. In step 610, a first respective port of the multi-position valve to the first canister is opened. Step 610 is similar to step 504, which is described above.

Method 600 continues with step 612. In step 612, the first respective port of the multi-position valve to the first canister is closed upon filling the first canister with the pressurized sample air. Step 612 is similar to step 512, described above.

Method 600 continues with step 614. In step 614, the UAS is positioned at a second position. Step 614 is similar to step 604, as described above. The second position may comprise at least one of a different altitude or a different geographical position from the first position.

Method 600 continues with step 616. In step 616, a second respective port to the second canister is opened. Step 616 is similar to step 610, as described above.

Method 600 continues with step 618. In step 618, the second respective port to the second canister is closed. Step 618 is similar to step 612, as described above.

In embodiments, method 600 may comprise further steps. For example, method 600 may further comprise step 602. In step 602, the UAS may be transferred to a first geographical location. The first geographical location may comprise the latitude and longitude of the first position. In embodiments, the UAS may be hovered at the first position and subsequently hovered at the second position, the first position and the second position comprising different altitudes at the first geographical location. In further examples, however, the UAS may be hovered at the first position and subsequently hovered at the second position, the first position and the second position comprising different geographical locations.

In embodiments, method 600 may further comprise step 606. In embodiments, the air sample collection apparatus 300 may further comprise an anemometer 132, and step 606 may comprise determining a wind direction and/or wind speed at the first position using the anemometer. In embodiments, the wind direction and/or wind speed measurements may further help determine VOC mass flux.

In further embodiments, the wind direction may be used to determine the location of the second position during sample collection. For example, the second position may be at least one of upwind or downwind with respect to the wind direction from the first position. This may help operators determine how VOCs detected are being transported in the atmosphere In embodiments, method 600 may further comprise step 608. In embodiments, the air sample collection apparatus 300 may further comprise a boom 134 comprising a coupled end 136 and a distal end 139, the anemometer being coupled to the distal end 139 of the boom 134. Step 608 may then comprise rotating the UAS 150 so that the boom 134 is parallel to the wind direction, which may provide higher quality data. In embodiments, the UAS 150 or air sampler 110 operator may rotate the boom 134 based on modeled or ground level wind direction data.

In embodiments, method 600 may further comprise step 622. In step 622, housekeeping data may be collected over at least one of a range of altitudes or a range of geographical positions, the housekeeping data comprising data from at least one of an ambient pressure sensor, an ambient temperature sensor, a relative humidity sensor, or an ambient relative humidity sensor. By collecting housekeeping data over at least one of a range of altitudes or a range of geographical positions, it may be possible to provide a better profile of background atmospheric conditions, providing context for the air samples collected.

The embodiments described herein may provide for a faster, higher resolution air sample collection system that can provide higher resolution VOC flux data.

The detailed descriptions of the above examples are not exhaustive descriptions of all examples contemplated by the inventors to be within the scope of the Application. Indeed, persons skilled in the art will recognize that certain elements of the above-described examples may variously be combined or eliminated to create further examples, and such further examples fall within the scope and teachings of the Application. It will also be apparent to those of ordinary skill in the art that the above-described examples may be combined in whole or in part to create additional examples within the scope and teachings of the Application. Accordingly, the scope of the Application should be determined from the following claims.

What is claimed is:

1. An air sample collection apparatus 300 comprising:
   a plurality of air canisters (102) comprising at least a first canister (104) and a second canister (106);

a multi-position valve (108) comprising an outlet (112), and an inlet region (114) fluidly connected to a plurality of ports (116), each respective port fluidly connected to a canister of the plurality of air canisters (102);

a pump (118) operable to provide pressurized sample air to the inlet region (114) of the multi-position valve (108); and a computing device (120) operable to open and close each respective port fluidly coupled to each canister (104, 106) of the plurality of canisters (102).

2. The air sample collection apparatus of claim 1, further comprising:

a check valve (122) fluidly coupled to the inlet region (114) of the multi-position valve (108), operable to exhaust fluid over a minimum crack pressure to an exhaust (124).

3. The air sample collection apparatus of claim 1, further comprising:

a sample pressure sensor (126) fluidly coupled to the inlet region (114) of the multi-position valve (108).

4. The air sample collection apparatus of claim 1, further comprising:

a flow meter (128) fluidly coupled to an exhaust end of a check valve (122), the flow meter jointly coupled to a common platform with at least one of the plurality of air canisters, the multi-position valve, the pump, or the computing device.

5. The air sample collection apparatus of claim 1, further comprising:

a GPS (130) jointly coupled to a common platform with at least one of the plurality of air canisters, the multi-position valve, the pump, or the computing device.

6. The air sample collection apparatus of claim 1, further comprising:

an anemometer (132) jointly coupled to a common platform with at least one of the plurality of air canisters, the multi-position valve, the pump, or the computing device.

7. The air sample collection apparatus of claim 6, further comprising:

a boom (134) comprising a coupled end (136) and a distal end (139), wherein the anemometer (132) is coupled to the distal end (139) of the boom (134) and the coupled end is coupled to the common platform.

8. The air sample collection apparatus of claim 7, wherein the boom (134) extends at least 4.5 feet from the coupled end (136) to the distal end (139).

9. The air sample collection apparatus of claim 1, wherein the plurality of canisters (102) further comprises at least a third canister (107), and the plurality of air canisters (102) are positioned in a circumferential arrangement.

10. The air sample collection apparatus of claim 1, further comprising:

a filter (138) coupled to an inlet (140) of the pump (118), operable to remove particles from the air entering the pump (118).

11. The air sample collection apparatus of claim 1, further comprising:

at least one of:
an ambient pressure sensor (142),
an ambient temperature sensor (144),
a relative humidity sensor (146), or
an ambient relative humidity sensor (146), wherein the at least one of the ambient pressure sensor, the ambient temperature sensor, the relative humidity sensor, or the ambient relative humidity sensor is jointly coupled to a common platform with at least one of the plurality of air canisters, the multi-position valve, the pump, or the computing device.

12. Method for collecting air samples using an air sample collection apparatus, the air sample collection apparatus comprising a plurality of air canisters including at least a first canister and a second canister, a multi-position valve comprising an outlet, and an inlet region fluidly connected to a plurality of ports, each respective port fluidly connected to a canister of the plurality of air canisters, a pump operable to provide pressurized sample air to the inlet region of the multi-position valve, and a computing device operable to open and close each respective port fluidly coupled to each canister of the plurality of canisters, the method comprising:

operating the pump to provide pressurized sample air to the inlet region of the multi-position valve;

opening a first respective port of the multi-position valve to the first canister;

upon filling the first canister with the pressurized sample air, closing the first respective port of the multi-position valve to the first canister;

opening a second respective port to the second canister; and upon filling the second canister with the pressurized sample air, closing the second respective port to the second canister.

13. The method of claim 12, further comprising:
positioning the air sample collection apparatus at a first position before opening the first respective port.

14. The method of claim 13, further comprising:
positioning the air sample collection apparatus at a second position before opening the second respective port.

15. The method of claim 12, wherein the air sample collection apparatus further comprises an anemometer jointly coupled to a common platform with at least one of the plurality of air canisters, the multi-position valve, the pump, or the computing device, and the method further comprises:

determining at least one of wind direction and wind speed data using the anemometer while the first respective port is open.

16. The method of claim 12, wherein the air sample collection apparatus further comprises a check valve fluidly coupled to the inlet region of the multi-position valve, operable to exhaust fluid over a minimum crack pressure to an exhaust.

17. The method of claim 12, wherein the air sample collection apparatus further comprises at least one of: an ambient pressure sensor, an ambient temperature sensor, a relative humidity sensor, or an ambient relative humidity sensor, the at least one of the ambient pressure sensor, the ambient temperature sensor, the relative humidity sensor, or the ambient relative humidity sensor being jointly coupled to a common platform with at least one of the plurality of air canisters, the multi-position valve, the pump, or the computing device, and the method further comprises:

determining a housekeeping data using at least one of the ambient pressure sensor, the ambient temperature sensor, the relative humidity sensor, or the ambient relative humidity sensor.

18. Method for collecting air samples using an air sample collection apparatus positioned on an unmanned aerial system (UAS), the air sample collection apparatus comprising a plurality of air canisters (102) including at least a first canister and a second canister, a multi-position valve comprising an outlet, and an inlet region fluidly connected to a plurality of ports, each respective port fluidly connected to a canister of the plurality of air canisters (102), a pump operable to provide pressurized sample air to the inlet region of the multi-position valve, and a computing device operable to open and close each respective port fluidly coupled to each canister of the plurality of canisters, the method comprising:

positioning the UAS at a first position;

opening a first respective port of the multi-position valve to the first canister;

upon filling the first canister with the pressurized sample air, closing the first respective port of the multi-position valve to the first canister;

positioning the UAS at a second position;

opening a second respective port to the second canister; and closing the second respective port to the second canister.

19. The method of claim 18, wherein the air sample collection apparatus further comprises an anemometer jointly coupled to a common platform with at least one of the plurality of air canisters, the multi-position valve, the pump, or the computing device, and the method further comprises:

determining a wind direction at the first position using the anemometer.

20. The method of claim 19, wherein the air sample collection apparatus further comprises a boom jointly coupled to a common platform with at least one of the plurality of air canisters, the multi-position valve, the pump, or the computing device, the boom comprising a coupled end and a distal end, wherein the anemometer is coupled to the distal end of the boom, and the method further comprises:

rotating the UAS so that the boom is parallel to the wind direction.

21. The method of claim 19, wherein the second position is at least one of upwind or downwind with respect to the wind direction from the first position.

22. The method of claim 18, further comprising:

transferring the UAS to a first geographical location before hovering the UAS at the first position and hovering the UAS at the second position, the first position and the second position comprising different altitudes at the first geographical location.

23. The method of claim 18, further comprising:

collecting housekeeping data over at least one of a range of altitudes or a range of geographical positions, the housekeeping data comprising data from at least one of an ambient pressure sensor, an ambient temperature sensor, a relative humidity sensor, or an ambient relative humidity sensor.

\* \* \* \* \*